(12) United States Patent
Christensen et al.

(10) Patent No.: US 12,365,931 B2
(45) Date of Patent: Jul. 22, 2025

(54) ASEPTIC DISSECTION AND CHARACTERIZATION OF MIXED MICROBIAL INFECTIONS, DISPLAY OF MICROBE SPATIAL RELATIONSHIPS AND LESION ADVANCING FRONTS IN HUMAN, VETERINARY, AND BOTANICAL SAMPLES

(71) Applicant: TRAC Research, Inc., Provo, UT (US)

(72) Inventors: Rella P. Christensen, Mapleton, UT (US); Brad J. Ploeger, Provo, UT (US); Kaesy Barker, American Fork, UT (US)

(73) Assignee: TRAC RESEARCH, INC., Provo, UT (US)

( * ) Notice: Subject to any disclaimer, the term of this patent is extended or adjusted under 35 U.S.C. 154(b) by 0 days.

(21) Appl. No.: 18/665,203

(22) Filed: May 15, 2024

(65) Prior Publication Data
US 2024/0376516 A1    Nov. 14, 2024

Related U.S. Application Data

(63) Continuation of application No. 18/664,267, filed on May 14, 2024.
(Continued)

(51) Int. Cl.
*C12Q 1/04* (2006.01)
*A61L 2/00* (2006.01)
(Continued)

(52) U.S. Cl.
CPC ............. *C12Q 1/04* (2013.01); *A61L 2/0088* (2013.01); *C12Q 1/025* (2013.01); *C12Q 1/06* (2013.01);
(Continued)

(58) Field of Classification Search
CPC . C12Q 1/04; C12Q 1/025; C12Q 1/06; C12Q 1/24; A61L 2/0088; G16B 35/10; G16B 35/20; G16H 50/20
(Continued)

(56) References Cited

U.S. PATENT DOCUMENTS

2024/0180981 A1*    6/2024    Ghaddar ............ A61K 31/4745

FOREIGN PATENT DOCUMENTS

| CA | 3002110 A1 * | 4/2017 | ............. G16B 10/00 |
| WO | WO-2018030838 A1 * | 2/2018 | ............ A23L 33/135 |
| WO | WO-2022226237 A1 * | 10/2022 | ............ A61K 31/282 |

OTHER PUBLICATIONS

Admin. "Aseptic Vs Sterile Environment: What a Dental Clinic Should be." 1-8. Web. Oct. 28, 2021. Retrieved from internet: https://www.melagautoclave.com.au/aseptic-vs-sterile/; p. 4.
(Continued)

*Primary Examiner* — Navin Natnithithadha
(74) *Attorney, Agent, or Firm* — Dorsey & Whitney LLP

(57) ABSTRACT

A system and method for novel processes of isolation, aseptic collection, genus-specie identification and quantification, and mapping of a restricted mixed microbe infection in living tissues in situ showing spatial distribution of the microbes within a sample of the living tissue. A tooth lesion or extraction socket and an endodontic entry excavation adjacent to an implant are examples of lesions resulting from such mixed microbe infections. The process may be incorporated into treatment procedures in a restricted area within hard or soft tissue, diagnostic techniques, minimizing failure of treatment processes, and validation of methods and products claiming antimicrobial or other properties in a treatment or preventive technique.

20 Claims, 14 Drawing Sheets

Related U.S. Application Data

(60) Provisional application No. 63/502,108, filed on May 14, 2023.

(51) Int. Cl.
  *C12Q 1/02* (2006.01)
  *C12Q 1/06* (2006.01)
  *C12Q 1/24* (2006.01)
  *G16B 35/10* (2019.01)
  *G16B 35/20* (2019.01)
  *G16H 50/20* (2018.01)

(52) U.S. Cl.
  CPC .............. *C12Q 1/24* (2013.01); *G16B 35/10* (2019.02); *G16B 35/20* (2019.02); *G16H 50/20* (2018.01)

(58) Field of Classification Search
  USPC ........................................................ 600/550
  See application file for complete search history.

(56) References Cited

OTHER PUBLICATIONS

Avon. "Oral Soft-Tissue Biopsy: An Overview." 1-9. JCDA. Web. Jul. 17, 2012.

Baek. "Characterization of intratissue bacterial communities and isolation of *Escherichia coli* from oral lichen planus lesions" 1-11. Scientific Reports. Web. Feb. 26, 2020.

Colgate. "Why Your Dentist Might Use a Rubber Dam." 1-9. Web. Jan. 9, 2023. Retrieved from Internet: https://www.colgate.com/en-us/oral-health/dental-visits/why-your-dentist-might-use-a-rubber-dam.

Demikrol. "Efficiency of HEPA-filtered extra-oral suction unit on aerosols during prosthetic dental preparation: A pilot study." 1937-1944. Clin Oral Investig. Web. Jan. 6, 2023.

Frank. "10 Ways to Stop Bleeding Gums." 1-9. Web. Feb. 2, 2023.

Hieken. "The Microbiome of Aseptically Collected Human Breast Tissue in Benign and Malignant Disease." 1-10. Scientific Reports. Web. Aug. 3, 2016.

Hogan. "Biopsy bacterial signature can predict patient tissue malignancy". 1-10. Scientific Reports. Web. Sep. 17, 2021.

Hudzicki. "Kirby-Bauer Disk Diffusion Susceptibility Test Protocol." 1-23. Web. Dec. 8, 2009.

Liefaard. "The Way of the Future: Personalizing Treatment Plans Through Technology." 12-23. Am Soc Clin Oncol Educ Book. Web. Apr. 1, 2021.

Patel. "A simple guide to using dental dam." 644-650. British Dental Journal. Web. May 28, 2021.

PCT/US2024/029343 International Search Report and Written Opinion dated Sep. 11, 2024.

Prime Dental Manufacturing. "Dental Dam". 1-2. Web. Dec. 31, 2020. Retrieved from the internet: https://www.primedentalmfg.com/whiten/dental-dam.

\* cited by examiner

400

Isolating an Area Surrounding the Lesion of Interest in Hard Tissue that can be Temporarily Dried and Preparing an Aseptic Field (Teeth), 405

Sterile Dissection of the Hard Tissue that can be Dried Temporarily in Sequentially Numbered Layers from the Lesion of Interest, From an Exterior of the Lesion Toward an Interior Extent of the Tissue to Define a Newly Exposed Surface in the Tissue, 410

Disinfecting the Newly Exposed Surface, 415

Sealing or Covering the Newly Exposed Surface with a Substance that Seals, 420

Isolating an Area Surrounding the Lesion of Interest in Hard or Soft Tissue that is Oozing or Bleeding, 505

Preparing an Aseptic Field Surrounding the Lesion of Interest while Allowing the External Surface to Remain Moist, 510

Sterile Sampling of Moist Fragments of the Hard or Soft Tissue that Oozes from the Lesion of Interest, from an Exterior of the Lesion Toward an Interior Extent of the Tissue, 515

Disinfecting the Lesion Surface with Antibiotic Powder or Liquid, 520

Closing the Soft Tissue over the Exposed Surface, 525

```
┌─────────────────────────────────────────────────────────────┐
│ Isolating a Lesion from a Healthy, Soft Tissue in a Body of │
│                    a Subject, 605                            │
└─────────────────────────────────────────────────────────────┘
                              ↓
┌─────────────────────────────────────────────────────────────┐
│ Preparing an Aseptic Field before Sterile Sampling the      │
│ Lesion From an Exterior to the Internal Area, 610           │
└─────────────────────────────────────────────────────────────┘
                              ↓
┌─────────────────────────────────────────────────────────────┐
│      Disinfecting with Antibiotic Powder or Liquid, 615      │
└─────────────────────────────────────────────────────────────┘
                              ↓
┌─────────────────────────────────────────────────────────────┐
│ Temporarily Covering the Newly Exposed Surface if           │
│                   Appropriate, 620                           │
└─────────────────────────────────────────────────────────────┘
```

FIG. 4

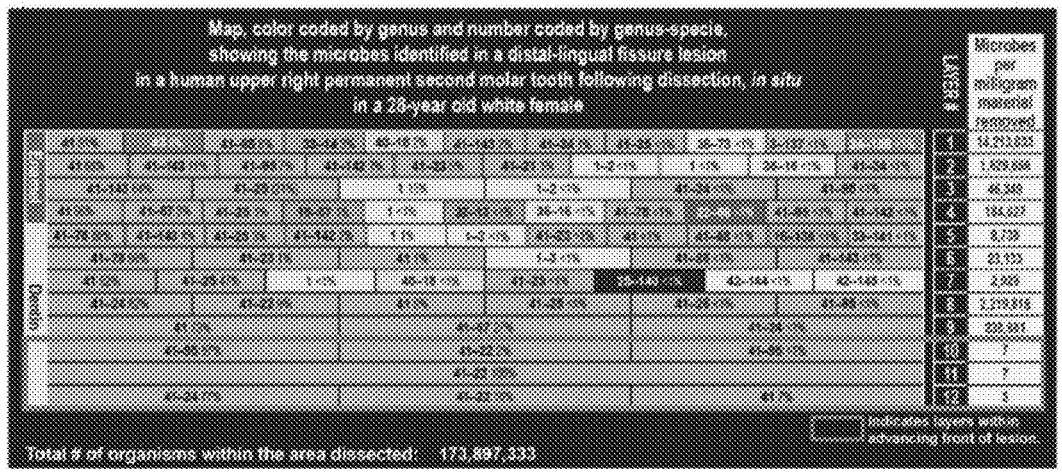
FIG. 5A
FIG. 5B
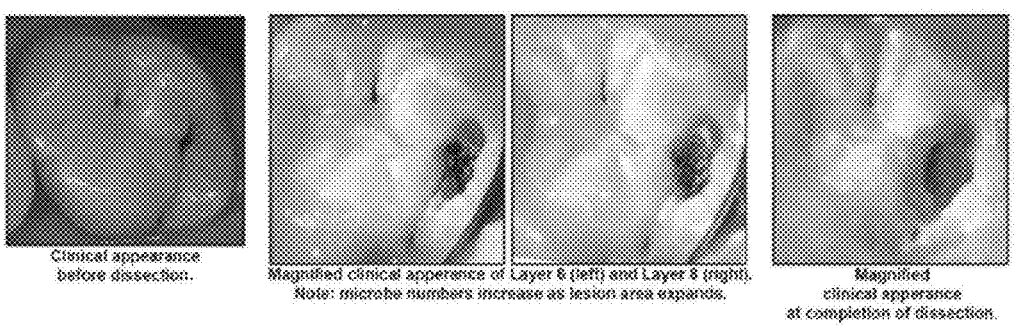
FIG. 5C

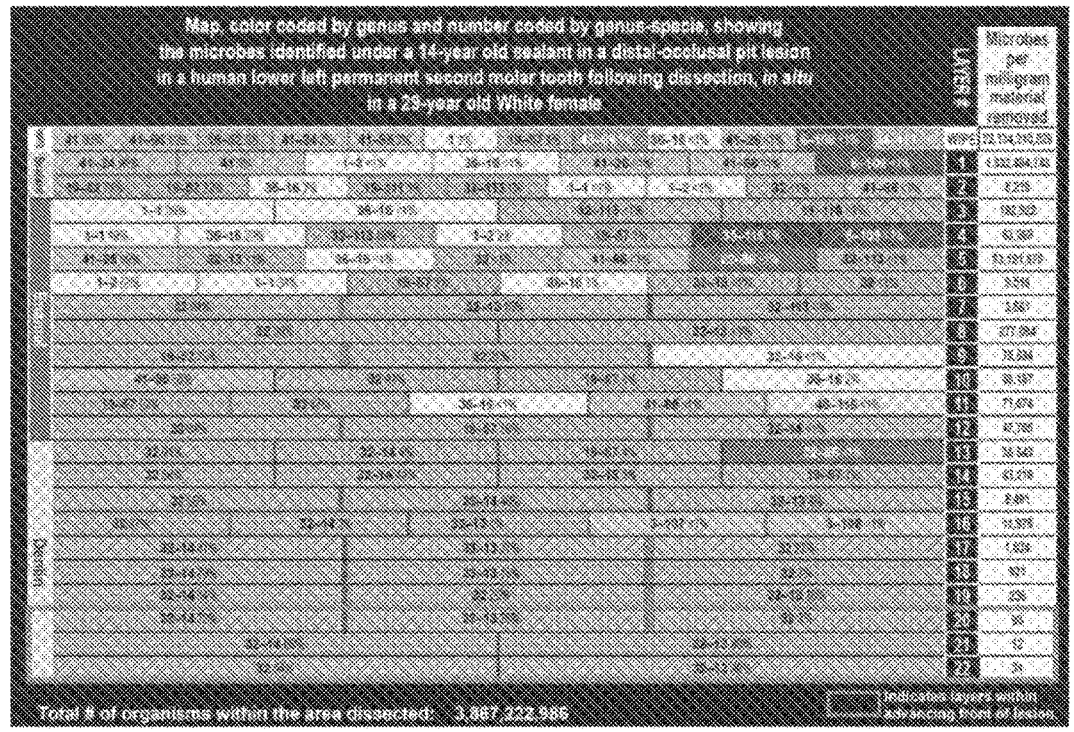

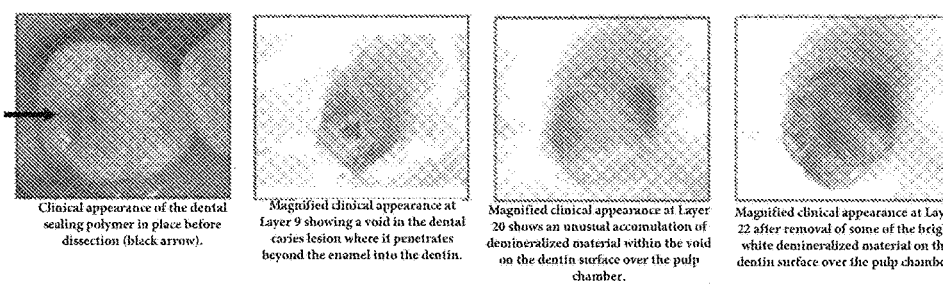

FIG. 7C

Clinical appearance of the dental sealing polymer in place before dissection (black arrow).

Magnified clinical appearance at Layer 9 showing a void in the dental caries lesion where it penetrates beyond the enamel into the dentin.

Magnified clinical appearance at Layer 20 shows an unusual accumulation of demineralized material within the void on the dentin surface over the pulp chamber.

Magnified clinical appearance at Layer 22 after removal of some of the bright white demineralized material on the dentin surface over the pulp chamber.

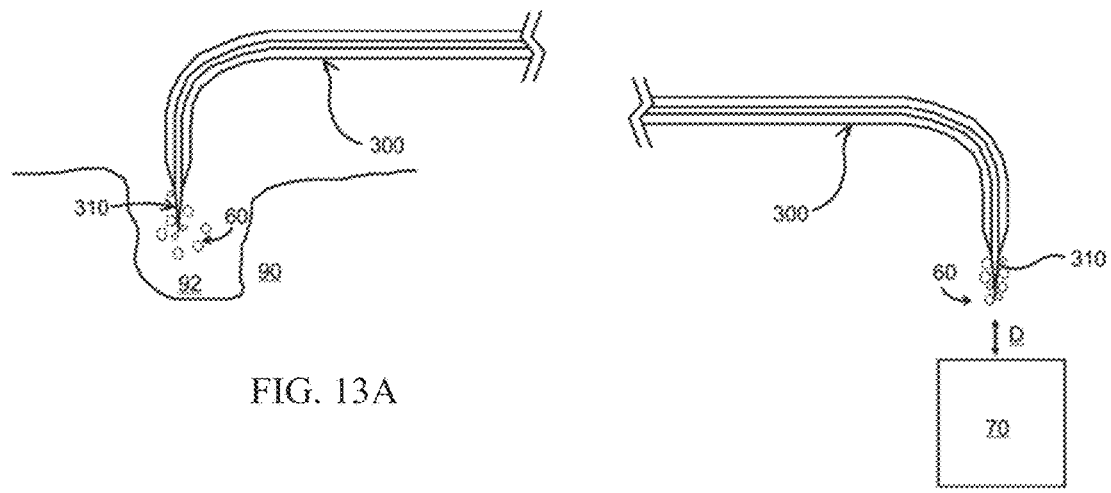
FIG. 13A
FIG. 13B
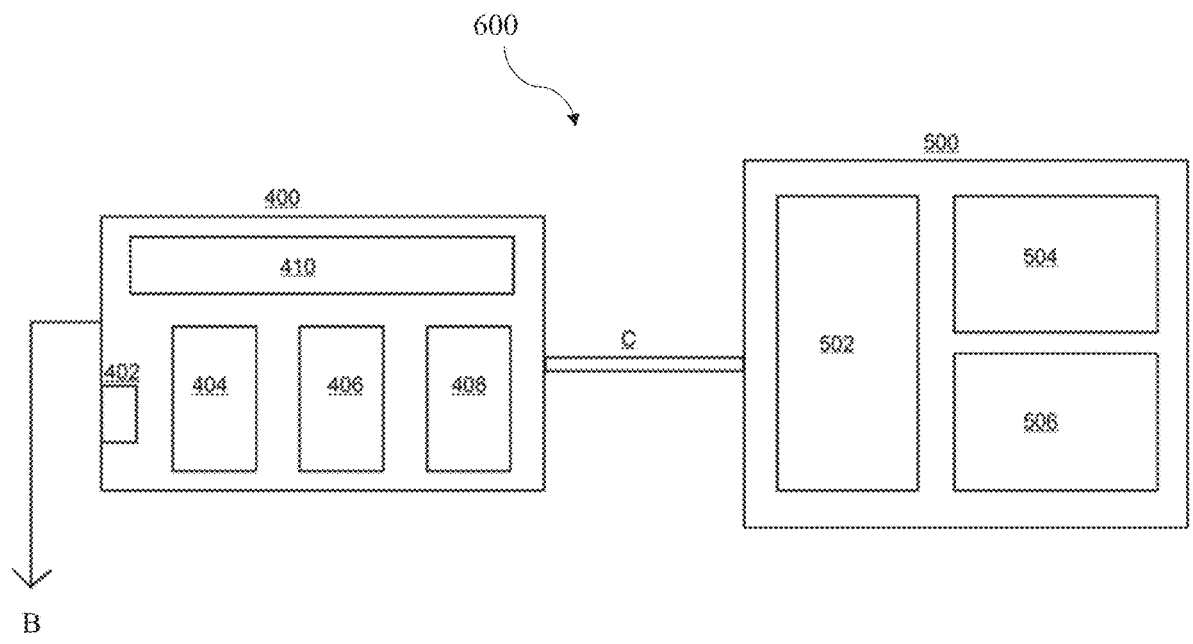
FIG. 14

800

```
┌─────────────────────────────────────────────────────────────┐
│ Licensed Clinician Places Antimicrobial Product per          │
│ Manufacturer's Directions, 805                               │
└─────────────────────────────────────────────────────────────┘
                              ↓
┌─────────────────────────────────────────────────────────────┐
│ Allow the Subject to Resume Normal Activities, 810          │
└─────────────────────────────────────────────────────────────┘
                              ↓
┌─────────────────────────────────────────────────────────────┐
│ Passage of a Predetermined Duration of Time, 820            │
└─────────────────────────────────────────────────────────────┘
                              ↓
┌─────────────────────────────────────────────────────────────┐
│ Re-Access the Site of the Antimicrobial Product using        │
│ Aseptic Systematic Layer-by-Layer Removal Method, 830       │
└─────────────────────────────────────────────────────────────┘
                              ↓
┌─────────────────────────────────────────────────────────────┐
│ Sample the Dissection Site for Microbes, 835                │
└─────────────────────────────────────────────────────────────┘
                              ↓
                    ◇ Are Microbes Present at ◇ ──Y──┐
                    ◇ the Dissection Site?, 840 ◇    │
                              │ N                    │
                              ↓                      │
┌─────────────────────────────────────────────────────┐│
│ The Purported Antimicrobial Product may be          ││
│ Validated as a Certified Antimicrobial Product, 845 ││
└─────────────────────────────────────────────────────┘│
                              ↓                      │
┌─────────────────────────────────────────────────────┐│
│ The Antimicrobial Properties of the Purported       │←┘
│ Antimicrobial Product are Deemed to be Suspect or   │
│ Ineffective, 850                                    │
└─────────────────────────────────────────────────────┘
```

FIG. 15

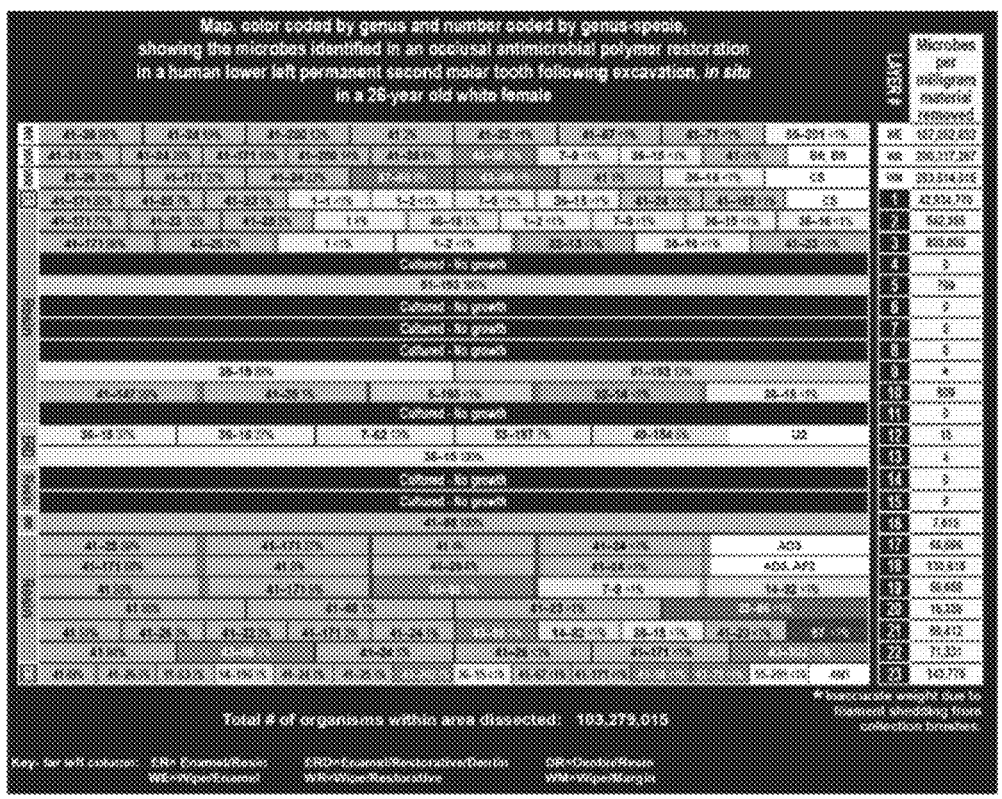
FIG. 16A
FIG. 16B
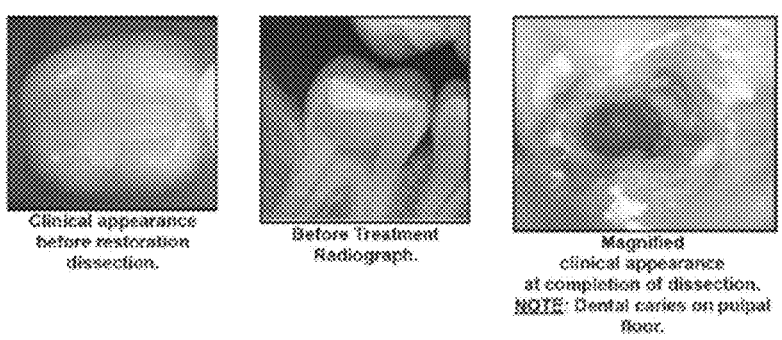
FIG. 16C

ASEPTIC DISSECTION AND CHARACTERIZATION OF MIXED MICROBIAL INFECTIONS, DISPLAY OF MICROBE SPATIAL RELATIONSHIPS AND LESION ADVANCING FRONTS IN HUMAN, VETERINARY, AND BOTANICAL SAMPLES

CROSS-REFERENCE TO RELATED APPLICATIONS

This application is a continuation of U.S. application Ser. No. 18/664,267 filed on May 14, 2024 and title "ASEPTIC DISSECTION AND CHARACTERIZATION OF MIXED MICROBIAL INFECTIONS DISPLAY MICROBE SPATIAL RELATIONSHIPS, AND LESION ADVANCING FRONTS IN HUMAN, VETERINARY, AND BOTANICAL SAMPLES" which claims priority to and the benefit of U.S. Provisional Application No. 63/502,108 filed on May 14, 2023 and title "SYSTEM AND METHOD FOR CHARACTERIZATION OF A MIXED MICROBIAL INFECTION IN A RESTRICTED OR LOCALIZED AREA OF HUMAN, VETERINARY, AND BOTANICAL TISSUE," the entire contents of which are herein incorporated by reference.

TECHNICAL FIELD

This disclosure relates generally to the removal of contents from mixed microbe lesions in a manner that allows characterization of the microorganisms, or microbes, within the lesions. For example, the treatment and dissection of dental lesions, such as dental caries, and to the identification of microorganisms within the dental lesions or bone or soft tissue lesions.

BACKGROUND

Lesions of microbial origin are among the oldest diseases known, and affect human, animal, and botanical tissues. Without any treatment of the diseased sites, these lesions can become disfiguring and are difficult and costly to treat in their later stages. In worst cases, these lesions can be fatal through spread of the local microbial infection to sensitive parts of the organism essential for life, such as the heart and brain in animals and the roots and cambium layer in botanical systems. Even with treatment, recurrence of microbial infections is common.

Both anciently and today, the most challenging infections of microbial origin are those caused when a group of microbes work together in a mixed microbe infection. These infections are the result of multiple different types and/or a variety of microorganisms (e.g., bacteria, multiple species and/or strains of bacteria, viruses, fungi, etc.). That is, rather than include one type of microbe, some lesions that result from microbial infections may be the result of multiple types of microorganisms acting in concert to degrade the tissue(s) where the lesion is found. However, human, animal, and botanical tissues also host a variety of important benign and/or helpful and even essential, microorganisms that may not contribute to a microbial infection in that organism.

Dental caries, also referred to as "cavities," are a type of dental lesion that infects and degrades a tooth. Dental caries are caused by undesirable microbial activity and are usually not diagnosed until destruction of the tooth has taken place visually or radiographically. At this point in the cavity's cycle, it can be too late for non-invasive treatments and, in some cases, the entire tooth may need to be removed.

Today, in place of the removed tooth, an implanted prosthesis can be positioned in the open socket space. However, despite removal of the infected tooth, if the microbial infection is not properly treated, the implant can suffer the same fate as the tooth, due to infection of the tissue surrounding the implanted prosthesis. Though it is known that the underlying microbial infection must be properly and fully dealt with, current treatments and techniques often slow, but do not stop the mixed microbe infections that cause the sequelae described.

SUMMARY

A method for analyzing a lesion of microbial origin in the tissue of a living host organism (e.g., a human, an animal, a plant, etc.) includes characterizing the microorganisms present in the lesion to determine its extent and possible cause. The extent of the microbial infection and the lesion it has caused can be determined in situ by this method. The microorganisms present in the microbial infection may also be identified in situ by this method. These acts may be performed without causing serious disfigurement of the living host organism.

Disclosed are methods, devices, and systems for determining microbes within the infected tissues and characterizing them by genus and specie name, concentrations present, and revealing their relative spatial positions within a lesion. Without limitation, such a method, device, or system may be used to treat and characterize a lesion present in hard tissues that can be dried temporarily, hard tissues and soft tissues that ooze and are best maintained as moist.

When a lesion is present in hard tissue that can be dried temporarily (e.g., a tooth), soft tissues may be retracted away from the lesion to optimize exposure of an access to the lesion. The portion of the lesion present on the surface of the hard tissue is then rendered dry by the isolation and exposure to HEPA filtered ambient air. A sterile barrier may then be applied around the borders of the lesion to seal to the dry tooth surface. The areas outside of the lesion may be disinfected without disinfecting the lesion in order to provide an aseptic environment. Then the lesion may be aseptically dissected, sequentially removing a layer of tissue at a time. The act of aseptically removing layers sequentially and preparing them for identification of the microbes within the removed material are then repeated until dissection is halted when two independent experts determine this point judging by tissue hardness, color, and proximity to the tooth's pulp chamber. The deepest layers of the lesion are of primary interest because they may define the boundary of the infection, or the advancing front of the lesion, and reveal the microbes that are sustaining the infection and driving the lesion forward. Once the lesion has been completely dissected, the newly exposed surfaces of the tissue may be disinfected to inactivate microbes deeply imbedded within the histological features of the tooth (e.g., dentin tubules). The goal is to prevent further infection or development of a secondary infection. In some cases, the deepest tissues may be sealed using materials that provide a true seal to dentin in teeth, such as conventional glass ionomer materials. Teeth are a non-limiting example of a hard tissue that may not ooze tissue fluids during the dissection, with a dental caries lesion comprising a non-limiting example of a lesion that may be present in a tooth.

When a lesion is present in hard or soft tissue that cannot be dried (e.g., hard tissue that bleeds or oozes fluid, such as bone and mucous membrane tissue, etc.), surrounding soft tissue may be retracted away from the lesion to optimize exposure of an access to the lesion. Due to the oozing, this type of lesion cannot be dissected by removing sequential layers, but its surfaces can be rendered temporarily damp for short periods of time and a limited number of specific sites may be sampled to determine the microbes present within the lesion. The sampling can be repeated a limited number of times (e.g., about 1-4 times, etc.). Locations of these samples are carefully planned in advance to define the boundaries of the lesion and locate the advancing front of the lesion to identify the microbes that are driving the infection forward. Once the lesion has been sampled, it may be treated with antibiotic in powder or solution form to prevent further infection. Some non-limiting examples of hard and soft tissues that cannot be dried include human and animal bone, mucous membrane, tree trunks, and the like.

In each of these embodiments of excavating a lesion from the tissue of a living host organism, newly exposed surfaces are defined in the tissue from which the lesion is removed. As indicated, the newly exposed surfaces may be disinfected. In the case of teeth in animals or humans, which are hard tissues that do not ooze or bleed, a solution comprising about 5% glutaraldehyde and about 35% hydroxyethyl methacrylate (HEMA) may be applied to the newly exposed surfaces to kill microbes that have advanced within histological features that make up the tooth (e.g., dentinal tubules).

An embodiment of a method involving a tooth may include isolating a lesion of interest from surrounding tissues, aseptically dissecting the lesion, and then determining whether microbes that caused the lesion are present. Determining whether microbes are present on or in the newly exposed surfaces may be conducted within a few minutes (e.g., within 30 min., within 15 min., within 10 min., within 5 min., within two minutes, within a minute, etc.) (i.e., substantially in real-time) or in real-time. This dissection, layer-by-layer, in hard tissues temporarily dried or using individual sampling sites in oozing tissues, may be repeated until no microbes are detected on newly exposed surfaces of the lesion or an acceptable number of microbes are detected on the newly exposed surfaces of the lesion in the tooth, followed by disinfection.

According to another aspect, this disclosure includes a method of generating a library of information (e.g., maps, data, etc.) on microbes in lesions from a particular type of tissue. As an example, a library of maps and data of microbes that have been dissected from human tooth lesions (cavities) may be generated. As another example, a library of maps and data of microbes that have been dissected from human periodontal bone tissue may be generated. Yet another example, a library of maps and data of microbes that have been dissected from human gums may be generated. Such a library may provide information that may be useful to researchers and clinicians seeking information on infection trends to design ways to stop these microbial infections. For example, researchers may analyze the data presented in a library of maps to identify the microbes that are frequently identified in lesions in a particular type of tissue among a particular population of subjects (e.g., in a particular part of the world, amongst a particular group of subjects, etc.). That information may then be used by researchers in efforts to identify how to reduce the occurrence of that type of lesion in the population, which may provide information useful to others, including clinicians, in practically reducing the occurrence of that type of lesion in the population. As another example, a comparison of a map of microbes in a lesion to a radiograph of the lesion may provide clinicians with information that may be helpful to them in excavating lesions from a tissue, while maximizing the removal of lesion-causing microbes from the tissue and minimizing the removal of microbe-free tissue and, thus, potential unneeded damage to the body of a subject.

Methods for validating the efficacy of purported antimicrobial products (e.g., an antimicrobial polymer restorative material, "filling", etc.) are another aspect of this disclosure. Such a method includes placement of a "filling" using the material by a licensed dentist in the body of a consenting subject in accordance with the manufacturer's directions in vivo. After waiting for a prolonged period of time, for example, months or even years, the "filling" is removed using the aseptic systematic removal layer-by-layer and sampling for microbial growth. If such sampling consistently (e.g., across a number of sites, subjects, etc.) reveals no microbes known to be active or dental caries disease are present within the treated site, the purported antimicrobial product may be validated as a certified antimicrobial product. If such sampling reveals that microbes known to be active in dental caries lesions are present, and in an unacceptably large number of cases, the purportedly antimicrobial product may be deemed to be suspect or ineffective.

Other aspects of the disclosed subject matter, as well as features and advantages of various aspects of the disclosed subject matter, should be apparent to those of ordinary skill in the art through consideration of the ensuing description, the accompanying drawings, and the appended claims.

BRIEF DESCRIPTION OF THE DRAWINGS

In the drawings:

FIGS. 1 through 4 are flowcharts of embodiments of steps in the methods for dissecting a lesion from tissue of a living host organism (human teeth in situ), characterizing a mixed microbial infection that has caused the lesion, and identifying the advancing front of one of the lesions;

FIG. 5A illustrates a first embodiment of a map of microorganisms identified after dissecting a lesion from a tissue of a living host organism;

FIG. 5B is a color-coded legend of the microorganisms represented by the map of microorganisms of FIG. 5A;

FIG. 5C illustrates a first lesion from which the map of FIG. 5A was generated following the method described and shows the appearance of the lesion at various stages in the layered dissection method;

FIG. 7A illustrates a third embodiment of a map of microorganisms identified while excavating a lesion from a tissue of a living host organism;

FIG. 7B is a color-coded legend of the microorganisms represented by the map of microorganisms of FIG. 7A;

FIG. 7C illustrates a third lesion from which the map of FIG. 7A was generated following the method described and shows the appearance of the lesion at various stages in the layered dissection method;

FIG. 10A shows the mesial and distal (or right and left) proximal surfaces of an extracted human cuspid tooth with clearly evident dental caries lesions;

FIG. 10B is a radiograph produced on a digital dental x-ray system;

FIG. 10C shows one half of the same tooth after longitudinal hemi-section;

FIGS. 13A and 13B illustrate use of the diagnostic tool of FIGS. 12A to 12C;

FIG. 14 schematically illustrates an embodiment of a system that includes the diagnostic tool of FIGS. 12A to 12C;

FIG. 15 is a flowchart illustrating a method for validating the efficacy of a purported antimicrobial product;

FIG. 16A illustrates an embodiment of a map of microorganisms identified following removal of a purported antimicrobial product from a tooth of a living person;

FIG. 16B is a color-coded legend of the microorganisms represented by the map of microorganisms of FIG. 16A; and FIG. 16C shows clinical images illustrating the inability of a dental material claiming antimicrobial properties to prevent microbe proliferation and development of frank dental caries on the pulpal floor after 16 months of service in the patient's oral cavity.

DETAILED DESCRIPTION

Figure 1:
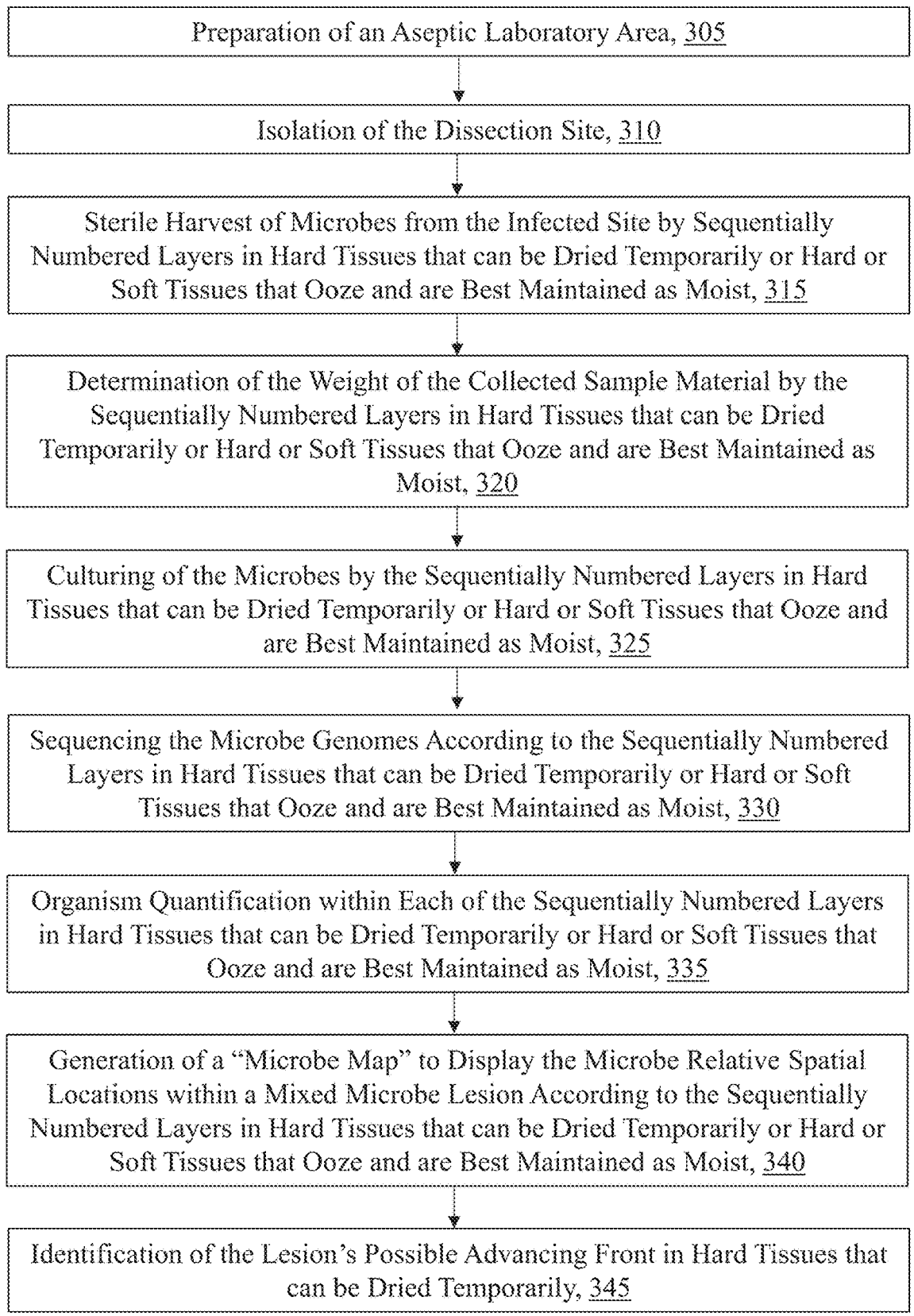

FIG. 1 is a flowchart of an embodiment of a method 300 for harvesting microorganisms from lesions and generating a map of microorganisms in the lesions. The method 300 includes general steps that may be performed regardless of the type of living host organism in which the lesion is present. Without limitation, the method 300 may be used to dissect a lesion and characterize a mixed microbial infection in a hard tissue that may be dried temporarily.

The method 300 includes, at reference 305, preparing the aseptic laboratory area, in which the method 300 is to be performed. More specifically, the method 300 may include preparing an aseptic laboratory area. Preparation of an aseptic laboratory area may include cleaning the area (e.g., air purification, disinfection of the treatment area surfaces, etc.); sterilization of equipment and instruments to be used in the remainder of the method 300 (e.g., cutting tools, motors, burs, blades, microscopes, etc.); and having personnel perform strict aseptic techniques (e.g., scrubbing; donning of appropriate apparel, such as gloves, masks, or the like; walking over sticky mats; etc.). All of the afore mentioned may prevent or minimize cross contamination while performing the remainder of the method 300, which may maximize the accuracy of an assessment of microorganisms present in a lesion and avoid contamination by extraneous microorganisms (e.g., microorganisms present in the laboratory area, microorganisms from the personnel performing the method 300, etc.).

Optionally, preparation of the treatment area at reference 305 includes obtaining samples from air and/or surfaces within the treatment area before performing the remainder of the method 300. The samples are cultured to create a control or "zero". Additional samples may be obtained during (e.g., once, at a plurality of times during, etc.) the method 300 and at the conclusion of the method 300 for comparative purposes and to confirm that the state of the treatment area is maintained while performing the method 300.

The method 300 may also include isolation of the dissection site, at reference 310 of FIG. 1. The manner in which the dissection site is isolated may correspond to the type of tissue in which the lesion is present. When the lesion is present in the mouth of a subject, isolation of the dissection site may begin with retracting lips, cheeks, tongue, etc., away from the lesion and proceed to use of a sterile material to seal the operating site against saliva leakage.

When the lesion is present in hard or soft tissue that bleeds or oozes, application of a material that seals may not be possible, so use of the layered dissection method may be modified to allow aseptic removal of small sections of the lesion at 2 to 4 pre-specified sites within the lesion.

When the lesion is present in hard tissue that can be dried temporarily, the tissue that surrounds the lesion may receive application of a sterile polymer barrier applied aseptically and built up to cover all areas surrounding the lesion to be dissected, leaving the lesion itself exposed. A sterile medium viscosity polymer that may be light-curable and/or may form a dam or other barrier around the area adjacent to the lesion may be used. Only the lesion and the area immediately adjacent to the lesion are left exposed. When correctly applied to a dry surface, the barrier seals against fluid (e.g., saliva, blood, etc.) leakage throughout the procedure, eliminating microbial contamination from these body fluids.

At reference 315 of FIG. 1, the method 300 includes aseptically removing a small amount of material from the surface of the lesion (e.g., numbered layers) repeatedly until a "stop point" is reached. For example, when the lesion is a dental caries in a tooth, the aseptic harvesting of microorganisms may include dissecting the lesion by layers with a bur or other instrument. The layer of the lesion may be removed with a very small sterile new carbide round bur (e.g., ⅛th round or ¼th round), which may be aseptically inserted into a sterile handpiece attachment and operated at very low speed to finely fragment a small amount (e.g., approximately 5 mg, etc.) of the lesion surface. The fragments may be picked up aseptically with sterile filaments of one or more sterile micro-brushes, which may be very small, pre-weighed, and numbered. As each micro-brush is filled to capacity with fragments, the micro-brush is transferred immediately and aseptically into an adjacent pre-weighed sterile letter-coded screw top tube containing pre-reduced sterile liquid medium. A plurality of sterile pre-weighed tubes containing pre-reduced sterile liquid medium may be used to collect fragments from the same layer. For hard and soft tissues that bleed or ooze, a sterile micro-brush may be used to collect samples from several sections of the lesion in a few (1-4) predetermined locations.

Once a pre-weighed letter-coded tube containing sterile medium has been filled with 1-4 pre-weighed number-coded brushes, a weight is determined (reference 320 of FIG. 1). The known weights of the collection tube(s), the pre-reduced sterile liquid medium, and the micro-brush(es) are subtracted from the total to determine the weight of the fragments from the most recently dissected layer of the tooth.

At reference 325 of FIG. 1, after weighing (e.g., immediately after weighing), the microorganisms are prepared for culturing. Each collection tube is transferred to another anaerobic chamber, where it is agitated (e.g., vortexed, etc.) and separated into two aliquots, with one designated for aerobic culturing and the other for anaerobic culturing. Contents from all the collection tubes receive serial 1:10 dilution in phosphate buffered saline (PBS) and an aliquot is spread onto CDC sheep blood agar in Petri plates that same day. For anaerobic samples, the PBS diluent and CDC sheep blood agar have been pre-reduced. Anaerobe chambers are operated at 10% $CO_2$, 10% $H_2$, 80% $N_2$.

As growth of the bacteria matures, each colony may be identified, at reference 330 of FIG. 1. All Petri plates are photographed. Colonies are prepared for lysing, extraction of ribosomal DNA (rDNA), and sequencing of the rDNA to identify the microbes from which the rDNA was obtained. Microbial rDNA may be isolated from the microbes of the colony using standard alkaline lysis and extraction methods. The isolated rDNA is amplified via polymerase chain reaction (PCR). Following PCR amplification, the rDNA may be sequenced and identified using sequencing techniques, such as 16s rDNA sequencing or another appropriate technique such as 16s rRNA. Remaining portions of all samples are prepared for cryo-storage.

In addition, at reference 335 of FIG. 1, each identified organism present in each numbered layer of the lesion is, or may be, quantified. The total combined aerobic and anaerobic organism counts are calculated using standard procedures of organism quantification used in microbiology:

$$\frac{\left[\frac{\text{count plate } A + \text{count plate } B}{2}\right] * \text{inverse of diluation of the Petri plates counted} * \text{initial volume of the sample}}{\text{volume plated on one Petri plate}}$$

The number of organisms per milligram of collected tooth material is determined and recorded for placement on the final lesion map along with its numbered dissection layer as follows:

$$\frac{\text{total organisms within a layer}}{\text{milligram tooth sample collected for the layer}}$$

Once each microorganism present in a layer of the lesion has been identified (at reference 330) and quantified (at reference 335), a "microbe map" of that lesion may be generated, at reference 340 of FIG. 1. The microbe map may identify relative spatial locations of microorganisms within a layer of a mixed microbe lesion in hard tissues that can be dried temporarily. The microbe map may include also a report of all of the viable microbes harvested (e.g., dissected, contained in all the removed samples, etc.) within the entire area dissected.

After a "layer" of hard tissues that can be dried temporarily or a "section" of oozing hard or soft tissues of the lesion are removed, all items used in the procedure are replaced with new sterile items and the process is repeated on another layer/section. The removal of another layer/section of the lesion occurs at reference 315 of FIG. 1, determination of a weight of the layer/section of the lesion occurs at reference 320 of FIG. 1, culturing of microorganisms in the layer/section occurs at reference 325 of FIG. 1, identification of each microorganism in the layer/section occurs at reference 330 of FIG. 1, quantification of each microorganism in the layer/section occurs at reference 335 of FIG. 1, and generation of a map of the layers/sections occurs at reference 340 of FIG. 1. The process may continue until a "stop point" is determined by two experts based on tissue hardness, color, and/or proximity to the tooth's pulp chamber. It may be determined once a layer/section of material that has been removed from the tissue substantially lacks or completely lacks infecting microorganisms (e.g., microorganisms that are not part of the normal flora of the tissue in which the lesion is present) to be determined by the real-time diagnostic instrument described in FIGS. 12, 13, 14. Such a layer/section may be identified as the possible advancing front of the lesion, at reference 345 of FIG. 1.

A final "lesion map" (i.e., microbe or microbial map) for each lesion is then created and coded (e.g., color-coded, greyscale-coded, etc.) by genus (or by genus/specie, or any other coding that may be helpful to answer questions about the lesion). FIGS. 5A, 6A, 7A, and 8A illustrate examples of maps of microbes in a lesion, while FIGS. 5B, 6B, 7B, and 8B illustrate example legends or keys to the maps of FIGS. 5A, 6A, 7A, and 8A, respectively. The percentage of each microbe present in each layer of the total number of microbes in the layer is also reported in each map. Additionally, the total number of microbes per milligram of material dissected from the lesion is listed for each layer in the far right column of each map and the total number of microbes within the area dissected is noted below the map. Using the example of the microbes contained within human dental caries lesions, data collected so far indicate the possible advancing front of the lesion appears to be the point at which the total number of microbes per milligram of dissected material removed drops significantly (e.g., to an order of magnitude of $10^2$ or less, etc.).

While dissecting a lesion from tissue, newly exposed surfaces are defined in the tissue. The method 300 of FIG. 1 may optionally include disinfecting the newly exposed surfaces of the tissue. Disinfecting can include disinfecting regions of the tissue beyond the newly exposed surfaces (e.g., dentin tubules that are present in undisturbed hard tissue of the teeth, etc.). Disinfecting may kill any remaining microbes that initially caused the lesion, preventing the emergence of a secondary lesion in the remaining tissue.

As another option, the method 300 may include sealing or covering the newly exposed surfaces of the tissue. Sealing or covering may also include regions of the tissue beyond the newly exposed surfaces. Sealing or covering the newly exposed surfaces may further include closing or filling a recess defined by dissecting the lesion.

Disinfecting and sealing may be conducted successively or concurrently. In embodiments where disinfecting and sealing occur concurrently, a single preparation may be applied to the newly exposed surfaces and, optionally, to surrounding surfaces of the hard or soft tissue to both disinfect and seal or cover these surfaces.

FIG. 2 is a flowchart illustrating an embodiment of a method 400 for treating a lesion of interest in hard tissue that can be dried temporarily. This is a more brief flowchart or summary of the main steps illustrated in the flowchart for method 300. The lesion may be a carious lesion. The method 400 may include isolating an area surrounding the lesion, at reference 405. Isolating an area of interest surrounding the lesion may include retracting soft tissues away from the lesion. Additionally, isolating the area of interest may include allowing the area surrounding the lesion to dry in HEPA filtered ambient air. Once the lesion is dry, isolating the area around the lesion includes providing a border on the area surrounding the lesion, the border extending completely around the lesion. For example, a dam (e.g., a dam made from a light-curable polymer) may be positioned or formed around the lesion to form the border. During the isolation process, the area surrounding the lesion and the border may be disinfected without disinfecting the lesion. Disinfection of the area surrounding the lesion and the border may aid in preventing contamination of the lesion by the microbes in the mouth of the patient.

The method 400 may include dissecting layers of hard tissue that can be dried temporarily from the lesion, from an exterior of the lesion toward an interior extent of the lesion to define newly exposed surfaces in the tissue, at reference 410 of FIG. 2. Layers may be dissected by drilling, slicing, or any other appropriate technique. In some embodiments, the exterior of a lesion may correspond to a surface of tissue in which the lesion is present (e.g., open facial dental caries lesions, see FIG. 6C). For example, in a tooth, the exterior of the lesion may correspond to a surface of the tooth. In other embodiments, a lesion may be confined within a tissue of a subject's body (e.g., a dental caries lesion on the proximal surface of the tooth root, which is below the gumline).

In some embodiments, dissecting the layers of hard tissue of the lesion continues to an internal extent of the lesion. As another non-limiting option, dissecting the layers of hard tissue of the lesion terminates short of a boundary of the hard tissue (e.g., the pulp chamber in the tooth). In teeth, the interior extent of the hard tissue corresponds to the border of the pulp chamber of the tooth. At the internal extent of the lesion, both the numbers and variety of microbes present drops dramatically, indicating the interior extent of the lesion may be near this point, and clinically further tissue removal may be halted and a disinfectant that penetrates the tooth may be used to eliminate deeper penetrating microbes. However, whether or not a disinfectant can be used at this point is dependent on whether the lesion is a hard tissue lesion that can be dried (e.g., a tooth, etc.) or is in oozing hard tissue (e.g., bone or soft tissue), which uses a different disinfectant (e.g., an antibiotic in powder or liquid form).

The dissected layers may be processed and evaluated to determine whether microbes are present in each dissected layer. For example, each layer may undergo collection, weighing, culturing, and/or sequencing to identify the microbes present in each layer, as described in reference to FIG. 1 (see references 315, 320, 325, and 330, respectively). The identified microbes may also be quantified to determine their respective numbers (e.g., by weight per mg of material) in each layer, and mapped, as described in reference to references 335 and 340, respectively, of FIG. 1. Additionally, the identified microbes may be compared layer-by-layer; for example, the microbes in one layer of a lesion may be compared with the microbes in one or more adjacent (e.g., preceding, subsequent, etc.) layers of the lesion.

The method 400 may also include disinfecting the newly exposed surfaces, at reference 415 of FIG. 2. Disinfecting can include disinfecting regions of the hard tissue beyond the newly exposed surfaces. Disinfecting may kill any remaining microbes that initially caused the lesion, preventing a secondary lesion in the remaining tissue.

The method 400 may also include covering the newly exposed (and now disinfected) surfaces that seals, at reference 420 of FIG. 2. Sealing or covering can include regions of the hard tissue beyond the newly exposed surfaces. Sealing or covering the newly exposed surfaces may include filling a recess defined by dissecting the lesion.

Disinfecting and sealing may be conducted concurrently or successively. In embodiments where disinfecting and sealing occur concurrently, a single preparation may be applied to the newly exposed surfaces and, optionally, to surrounding surfaces of the hard tissue to both disinfect and seal or cover these surfaces. An example of such a preparation is a solution of about 5% glutaraldehyde and about 35% hydroxyethyl methacrylate (HEMA).

Turning now to FIG. 3, a flowchart of an embodiment of a method 500 for treating a lesion of interest in hard or soft tissue that may ooze or bleed is provided. The method 500 may include isolating an area surrounding the lesion, at 505. As before, isolating the area surrounding the lesion may include retracting soft tissues. As the lesion is present in hard or soft tissue that may ooze or bleed, drying the lesion and/or area surrounding the lesion may include removing excess saliva, blood, or other bodily fluids without fully drying the surface. The lesion, or the area surrounding the lesion would be allowed to remain "moist" (e.g., purposely allowed to remain slightly wet).

The method 500 may also include disinfecting the area surrounding the lesion without disinfecting the lesion using an antibiotic in powder or solution form, as in reference 520 of FIG. 3.

Collection of moist hard tissue fragments (e.g., bone), weighing, culturing, and/or sequencing to identify the microbes present in each section, as described in reference to references 315, 320, 325, and 330, respectively, of FIG. 1. The identified microbes may also be quantified to determine their respective numbers (e.g., by weight per mg of material) in each section, as described in reference to reference 335 of FIG. 1, and mapped, as described in reference to reference 340 of FIG. 1. Additionally, the identified microbes may be compared section-by-section; for example, the microbes in one section of a lesion may be compared with the microbes in one or more adjacent (e.g., preceding, subsequent, etc.) sections of the lesion.

The method 500 may also include disinfecting the newly exposed surfaces, at reference 520 of FIG. 3. Disinfecting can include disinfecting regions of the hard or soft tissue beyond the newly exposed surfaces. Disinfecting may kill any remaining microbes that initially caused the lesion, preventing a secondary lesion in the remaining tissue. Disinfecting may be accomplished with an antibiotic in powder or in solution form.

The method 500 may also include sealing or covering the newly exposed (and now disinfected) surfaces, at reference 525 of FIG. 3. Sealing or covering can include closing regions of the hard or soft oozing tissue beyond the newly exposed surfaces and/or closing the newly exposed surfaces by filling a recess defined by sampling the lesion (e.g.; in bone).

Disinfecting and sealing may be conducted successively or concurrently. In embodiments where disinfecting and sealing occur concurrently, a single preparation may be applied to the newly exposed surfaces and, optionally, to surrounding surfaces of the hard or soft oozing tissue to both disinfect and seal these surfaces.

FIG. 4 is a flowchart of an embodiment of a method 600 of sampling a lesion of interest from soft tissues (e.g., gums, skin, etc.). The method 600 may include isolating the lesion from healthy tissue in a body of a subject, at reference 605. Similar to the methods 300, 400, and 500 of FIGS. 1, 2, and 3, respectively, and isolating the lesion may include retracting surrounding tissues and partially drying areas surrounding the lesion (e.g., leaving the lesion moist). As the lesion is within soft tissue, drying the area surrounding the lesion may include removing excess saliva or other bodily fluids without fully drying the surface, the lesion, or the area surrounding the lesion, and may be repeated while performing the method 600.

The method 600 may include application of a sterile material or disinfecting areas surrounding the lesion to provide an aseptic environment before sampling the lesion.

The method 600 also includes sampling from the soft tissue lesion, at reference 610 of FIG. 4. Sampling the lesion defines new surfaces in the soft tissue.

The samples may be processed and evaluated to determine whether microbes are present in each sample. Each sample may undergo collection, weighing, culturing, and/or sequencing to identify the microbes present in each sample, as described in references 315, 320, 325, and 330, respectively, of FIG. 1. The identified microbes may also be quantified to determine their respective numbers (e.g., by weight per mg of sample collected), as described in reference to reference 335 of FIG. 1, and mapped by sample as described in reference to reference 340 of FIG. 1. Additionally, the identified microbes may be compared section-by-section; for example, the microbes in one section of a lesion may be compared with the microbes in one or more adjacent (e.g., preceding, subsequent, etc.) sections of the lesion.

The method 600 may also include disinfecting the soft tissue lesion, at reference 615 of FIG. 4. Disinfecting can include disinfecting soft tissue beyond the sampled surfaces. Disinfecting may kill any remaining microbes that initially caused the lesion, preventing a secondary lesion in the remaining tissue.

The method 600 may also include temporarily covering the newly exposed (and now disinfected) surfaces, at reference 620 of FIG. 4. The newly exposed surfaces may be temporarily covered. Regions of the soft tissue beyond the sampled surfaces may be covered. Temporary covering may include use of a glue or similar materials.

Disinfecting and covering may be conducted successively or concurrently. In embodiments where disinfecting and sealing occur concurrently, a single preparation may be applied to the sampled surfaces and, optionally, to soft tissue surrounding the sampled surfaces.

FIG. 5A is an embodiment of a map of microbes generated during or after a dissection process, such as the dissection processes of methods 300, 400, 500, and/or 600 of FIGS. 1, 2, 3, and 4, respectively. FIG. 5B provides an example of a legend or key to the microbes by coding (e.g., color coding, greyscale coding, etc.) and genus-specie numbers. FIG. 5C illustrates the lesion (e.g., a dental caries lesion) from which the map of FIG. 5A was generated. Specifically, the map is generated following processing, culturing, and identification of each layer dissected from the lesion. Each layer is analyzed for the microbes (e.g., genus and/or specie) and their numbers per milligram of tooth material removed in the layer. The generated microbe map provides a visual representation of the microbe taxa present, their numbers, their relative spatial positioning by layer number within the lesion (i.e., which layer they were found in), the percentage each viable microbe taxa contributes to the total number of microbes in the layer. The microbe map includes the first layer (e.g., at a surface of the lesion, etc.) and all subsequent, adjacent layers of the lesion.

The microbes included in the microbe map of FIG. 5A are identified and coded by identification (e.g., genus and/or specie names). That is, every microbe present in the lesion is assigned an identifier (e.g., color, shade of grey, etc.) unique to its genera, and appears in the map within the layer that corresponds to the dissection layer number assigned during the dissection process.

Figures 6A, 6B, 6C:
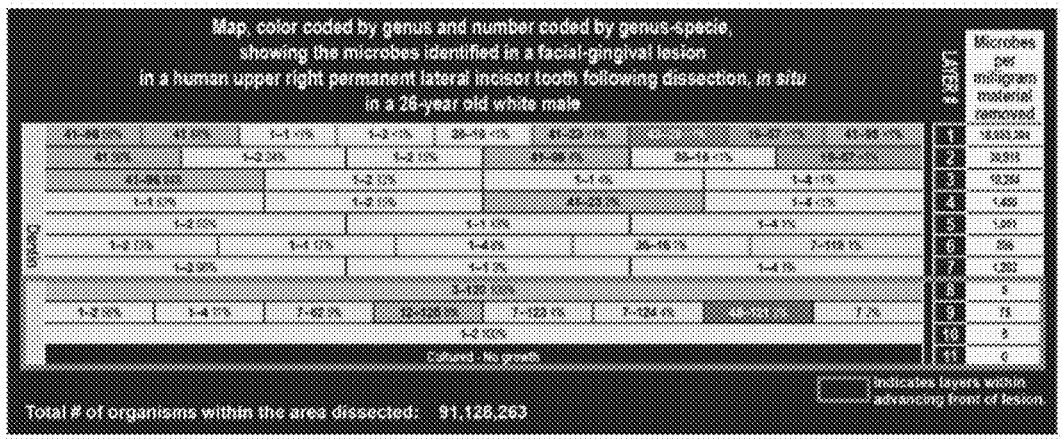
FIG. 6A illustrates a second embodiment of a map of microorganisms identified after dissecting a lesion from a tissue of a living host organism.
FIG. 6B is a color-coded legend of the microorganisms represented by the map of microorganisms of FIG. 6A.
FIG. 6C illustrates a second lesion from which the map of FIG. 6A was generated following the method described and shows the appearance of the lesion at various stages in the layered dissection method.

FIG. 6A illustrates another embodiment of a map of viable microbes present in a lesion-another dental caries lesion. FIG. 6B is a coded legend of the microbes represented in the map of FIG. 6A. FIG. 6C illustrates the dental caries lesion from which the map of FIG. 6A was generated at various stages of its layered dissection. More specifically, FIG. 6C shows the clinical appearance of an upper lateral incisor tooth before treatment, during dissection, and at completion of the dissection to correlate the clinical appearance of the tooth with the microbe data.

The center portion of the map of FIG. 6A uses coding (e.g., a color, a shade of grey, etc.) and a bold hyphenated number to identify each microbe present in each dissected layer of the lesion. Note the predominance of microbes of the genus *Actinomyces* in the central part of the lesion in FIG. 6A. The percent of each microbe present in each layer of the lesion is shown in the non-bolded number. The column at the far left indicates the material dissected as the dissection moves from a first layer of the lesion (e.g., the outer surface of the lesion, etc.) to a last layer of the lesion (e.g., the inner surface of the dentin of the tooth, against the pulp chamber of the tooth, etc.). The columns at the far right list in sequential numbering the layers removed, and a substantially accurate estimation of the number of microbes per milligram (mg) by layer according to current standard microbiology methods. Note the microbes decrease in variety and number as the depth of the dissection increases. The red rectangle outlines the layers within the possible advancing front starting at Layer 8. Layer 11 shows that viable microbes were not cultured at the point where the dissection was halted to avoid exposure of the pulp chamber of the tooth. The total number of microbes within the area dissected is indicated in white type at the bottom of the map of FIG. 6A.

FIG. 7A illustrates another embodiment of a map of viable microbes present in a lesion. This lesion shows failure of a dental "sealant" polymer material placed 14 years earlier to try to prevent the tooth decay that developed later. FIG. 7B is a coded legend of the microbes in the map of FIG. 7A. FIG. 7C illustrates the dental lesion from which the map of FIG. 7A was generated. More specifically, FIG. 7C shows the clinical appearance of a lower molar tooth of a human before treating the dental caries lesion, and at various layers in the progression of the dissection.

As with the maps of FIGS. 5A and 6A, the center portion of the map of FIG. 7A uses coding (e.g., color, a shade of grey, etc.) and a bold hyphenated number to identify each microbe present in a layer that has been dissected from the lesion. Note the predominance of microbes of the genus *Propionibacterium* in the central part of the lesion, and the complete dominance of this genus from layer 17 through the area of the possible advancing front of the lesion. The percent of each taxa present in each layer of the lesion is shown in the non-bolded number. The column at the far left indicates the material dissected from the outer surface to the innermost area of the lesion, and includes microbes cultured from a sterile brush used to wipe the outer surface, microbes within the dissected "sealant" polymer, the tooth's dissected enamel, and the tooth's inner dentin. The columns at the far right list in sequential numbering the layers removed, and a substantially accurate estimation of the number of microbes per milligram (mg) by layer according to current standard microbiology methods. Note the microbes decrease in variety and number as the depth of the dissection increases. The rectangle outlines the layers within the possible advancing front, starting at Layer 20. Layer 22 shows that microbes were still present when dissection was halted to avoid exposure of the pulp chamber within the tooth. The total number of microbes within the area dissected is indicated in white type at the bottom of the map of FIG. 7A.

Figure 8A:
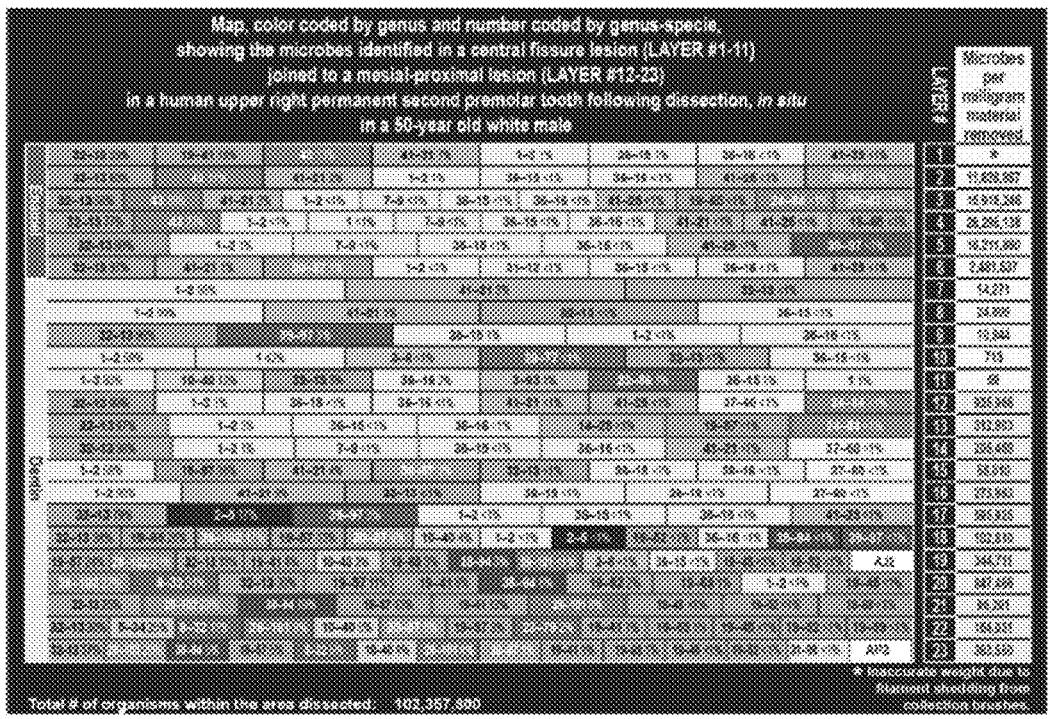
FIG. 8A illustrates a fourth embodiment of a map of microorganisms identified while excavating a lesion from a tissue of a living host organism.
Figure 8B:
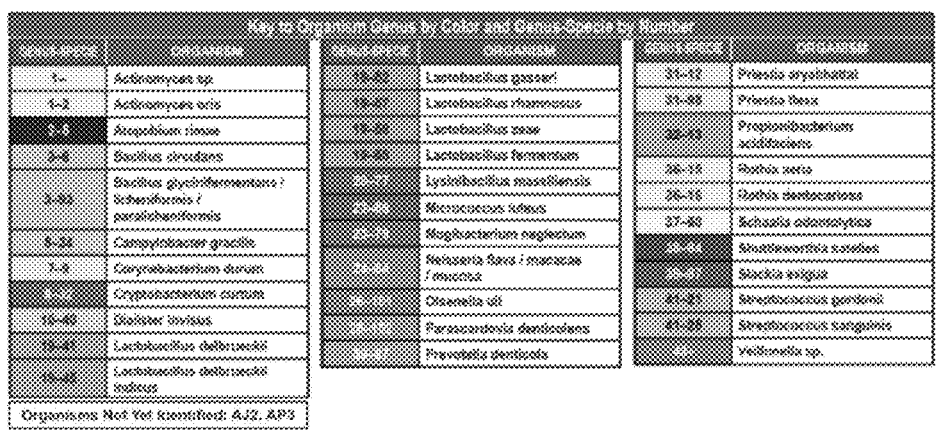
FIG. 8B is a color-coded legend of the microorganisms represented by the map of microorganisms of FIG. 8A.
Figure 8C:
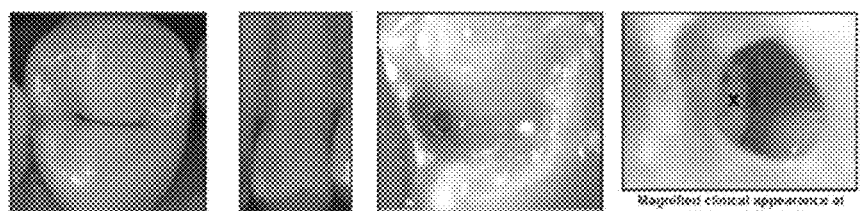
FIG. 8C illustrates a fourth lesion from which the map of FIG. 8A was generated following the method described and shows the appearance of the lesion at various stages in the layered dissection method.

FIG. 8A illustrates another embodiment of a map of viable microbes present in another dental caries lesion. This lesion appears visually far more simple than indicated by the radiograph or in the layered dissection. FIG. 8B is a coded legend of the microbes in the map of FIG. 8A. FIG. 8C illustrates the dental lesion from which the map of FIG. 8A was generated. More specifically, FIG. 8C shows the clinical appearance of an upper premolar in a human before treating the dental caries lesion, followed by images of the extensive involvement of the decay of the tooth as two different lesions starting in two different surfaces of the tooth intersect at layers 11-12 and display different microbe profiles and concentrations that penetrate into the pulp chamber of the tooth.

The map of FIG. 8A uses coding (e.g., color, a shade of grey, etc.) and a bold hyphenated number to identify each taxa present in each layer dissected. Note there is no obvious predominant microbe by genus percentage throughout, or in any layer of the lesion. The percent of each microbe present in each layer of the lesion is shown in the non-bolded number. The column at the far left indicates the material dissected as the dissection moves from a first layer of the lesion (e.g., the outer surface of the lesion) to a last layer of the lesion. The columns at the far right list in sequential numbering the layers removed, and a substantially accurate estimation of the number of microbes per milligram (mg) by layer according to current standard microbiology methods. The total number of microbes within the area dissected is indicated at the bottom of the map of FIG. 8A.

Figure 9:
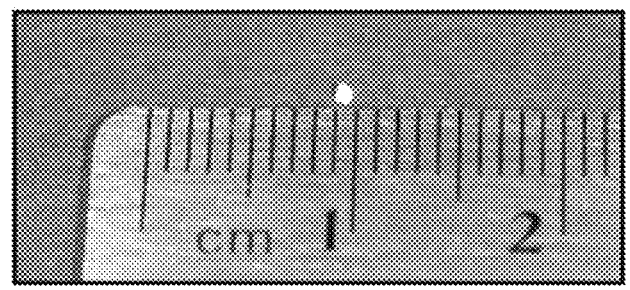
FIG. 9 illustrates a tooth fragment.

FIG. 9 illustrates a fragment of a human tooth. The fragment is spherical with a diameter of about 1 mm and a weight of 1 mg. The numbers reported by layer in the "Organisms per mg" column in the maps of FIGS. 5A, 6A, 7A, and 8A represent the number of microbes in that layer, normalized to the milligram standard. The actual number of microbes in the layer may be many times the numbers reported per milligram of weight. An estimation of the total number of microbes within the total area dissected is shown at the bottom of each map. These numbers indicate a range from about $1 \times 10^8$ to about $4 \times 10^9$ microbes within the areas of the lesions dissected that are represented by the maps of FIGS. 5A, 6A, 7A, and 8A. These high microbial populations can be attributed to several factors. These factors can include either or both of the following: (1) new microbes are introduced continuously by anything humans or other animals place into their mouth; (2) the oral cavity has an ideal environment (warm, moist, nutrient rich) which sustains the microbes well and encourages multiplication, etc.

Figure 10:
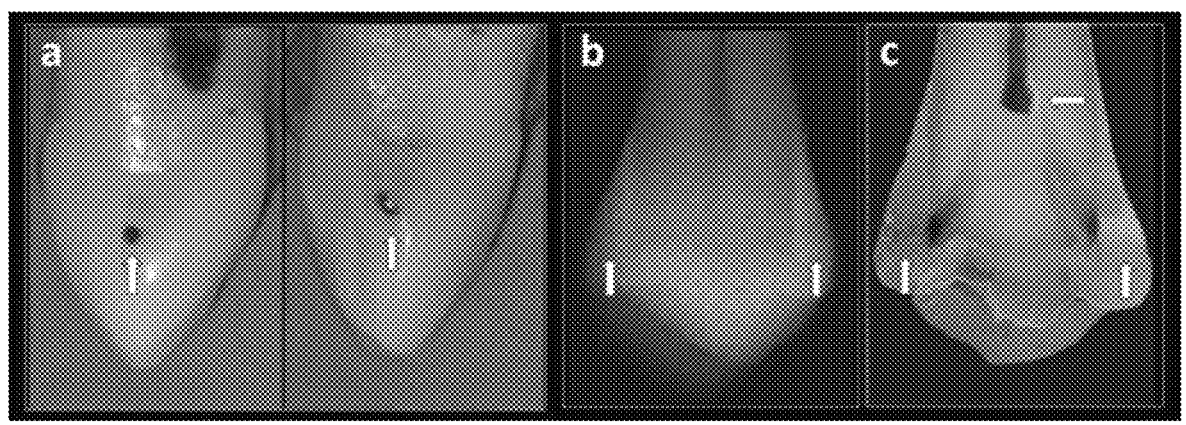
FIG. 10 illustrates comparisons of a dental lesion visually and through radiographic or other imaging.

FIG. 10 illustrates comparisons of a dental lesion visually and through radiographic or other imaging, illustrating the challenges clinicians face when using clinical signs (e.g., discoloration, increased porosity, increased softness, etc.) to judge the extent of dental caries lesions. For example, the clinical signs used by clinicians may include surface appearance of the tooth and the lesion(s) therein and the use of radiographic images, neither of which can consistently provide an accurate assessment of the boundaries, extent, or progression of a dental caries lesion within a tooth. Radiographs give only an indication of the extent of the damage caused by the microbes. Radiographs typically reveal areas of the tooth that have decayed. They do not show areas where the microbes and/or their byproducts have spread within the tissues of the tooth that have not yet decayed.

FIG. 10A shows the mesial and distal (or right and left) proximal surfaces of an extracted human cuspid tooth with clearly evident dental caries lesions (see white arrows). FIG. 10B is a radiograph produced on a digital dental x-ray system of this same tooth. Locations of the radiograph where the dental caries lesion demineralized the enamel of the tooth are a slightly darker shade of grey than non-affected areas of the enamel (see white arrows). FIG. 10C shows one half of the same tooth after longitudinal hemi-sectioning. The lower two white arrows point to the dental caries lesions extending through the enamel on the left and right sides of the tooth. The image shows clearly the dentin underlying the enamel layer has been penetrated, which is indicated by the dark brown and light brown areas extending upward towards the tooth's pulp chamber. The light brown of the dentin shows the migration of the microbe infection following the dentinal tubule structure of the tooth. The horizontal white arrow near the top of the image points to the bright white severe demineralization on the wall of the pulp chamber of the tooth, indicating that the demineralization extended through the enamel and dentin and reached the wall of the pulp chamber. The radiograph of FIG. 10B does not show the extent of the lesion or provide any information on the microbes present within the lesion.

If a clinician relies on clinical signs and/or radiographic images to excavate a lesion, the clinician will often remove only the outer portion of the lesion. By relying on the clinical signs and/or a radiograph, viable microbes may remain in the tooth. Thus, the lesion may, and often does, recur adjacent to the excavated area (e.g., tooth preparation and/or border of the "filling"). This recurrence is called "secondary caries." FIG. 7C shows a clinical example of secondary caries below a pit and fissure sealant (e.g., a resin polymer material, etc.). In this case, the clinical appearance of a dental caries lesion that has developed around and under the sealant is displayed in the image as subsurface discoloration. The sterile harvest method described herein demonstrates that the microbes that cause a dental caries lesion may penetrate well beyond the areas showing clinical signs of infection and/or the appearance of the lesion in a radiograph. When the lesion was dissected as described herein, in which layers of the lesion were numbered and cultured, extremely large numbers of viable microbes were found. FIG. 7A shows the organisms cultured and identified by rDNA sequencing, the identification of each microbe present within each layer, and the percentage of each microbe present within each layer of the lesion. The extremely high number of microbes present in only 1 mg of removed "sealant" material in this example lesion (1,332,494,743) is noteworthy.

Maps of the type shown in FIGS. 5A, 6A, 7A, and 8A and their accompanying legends shown in FIGS. 5B, 6B, 7B, and 8B and data from such maps and legends may be collected in a library of maps of lesions. As an example, a library may include information on the microbes that were present in human tooth lesions that have been dissected in situ. As another example, a library may include information on the microbes that were present in lesions that have been dissected from human bone tissues. As yet another example, a library may include information on microbes that were present in lesions from human or animal gums. Such a library may be organized in a variety of ways. For example, such a library may be organized by types and sub-types of tissues, types of lesions in each tissue, demographic factors (e.g., gender, age, geographic location, economic status, religion, etc.), or the like. As a library of maps and data from dissections of a certain type of lesion (e.g., dental caries lesions, etc.) from a certain type of tissue (e.g., teeth, etc.) grows, the maps and the data may provide information that may be useful to researchers and clinicians. For example, it could be used to train an artificial intelligence (AI) diagnostic instrument that indicates the efficiency of a tooth preparation disinfectant, or tells the clinician how deeply to excavate by indicating when all viable microbes have been removed.

Researchers may analyze the data presented in a library to identify the microbes that are primarily responsible for lesions in a particular type of tissue among a particular population of subjects (e.g., in a particular part of the world, amongst a particular group of subjects, etc.). That information may then be used by researchers in efforts to identify how to reduce the occurrence of that type of lesion in the population, which may provide information useful to others, including clinicians, in practically reducing the occurrence of that type of lesion in the population.

As another example, a comparison of a map of microbes in a lesion to clinical signs and/or a radiograph of the lesion may provide clinicians with information that may be helpful to them in excavating lesions from a tissue, while maximizing the removal of lesion-causing microbes from the tissue and minimizing the removal of healthy tissue and, thus, potential damage to the body of a subject.

Figure 11:
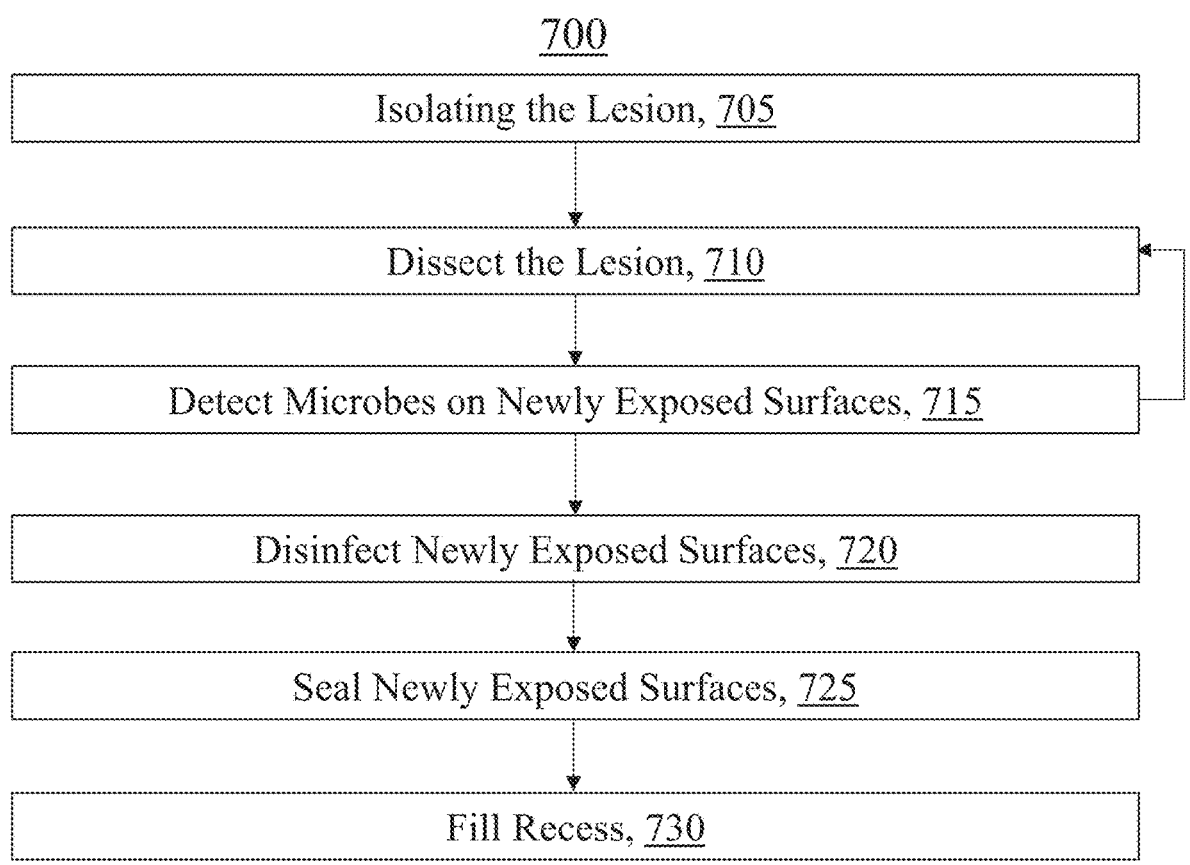
FIG. 11 is a flowchart illustrating a method for excavating a dental caries lesion from a tooth.

Turning now to FIG. 11, an embodiment of a method 700 of dissecting a lesion in a tooth, including substantially all or all of the microbes that caused the lesion, from a tissue (e.g., a hard tissue that can be dried temporarily or a hard or soft tissue that oozes or bleeds) is depicted. The method 700 may include isolating the lesion from surrounding tissues, at reference 705.

Once the lesion has been isolated from surrounding tissues, a section of the lesion may be aseptically dissected at reference 710. Dissection of the section of the lesion may be guided by conventional clinical factors, such as discoloration, increased porosity, and/or increased softness of the tissue caused by the lesion, radiographic images that show damage caused by the lesion, or the like.

Once the section of the lesion is dissected, testing of the newly exposed surfaces of the tissue in which the just-dissected section of the lesion was present may occur to determine whether microbes that caused the lesion are still present in the tissue, at reference 715 of FIG. 11. Such a determination may be made in any suitable manner (e.g., by sampling using aseptic technique, use of an AI diagnostic instrument, etc.) and may occur in within a matter of minutes (e.g., within 30 min., within 15 min., within 10 min, within 5 min., within 2 min, within 1 min., etc.) or even in seconds, substantially in real-time, or in real-time. For example, a rapid assay, such as a lateral flow assay, a biosensor (e.g., a portable ATP fluorescence detector, etc.), or the like, for one or more microbes that are known to cause lesions of the type being dissected may be used.

If a sufficient microbial load is detected on or in any of the newly exposed surfaces, the acts of dissecting another section of the lesion, at reference 710, and determining the presence of microbes on newly exposed surfaces of the tissue, at reference 715, may be repeated. More specifically, these acts may be repeated until a microbial load detected on or in the newly exposed surfaces at reference 715 is at an acceptable level.

Once the acts of dissecting at reference 710 of FIG. 11 and determining whether microbes are present on or in newly exposed surfaces at reference 715 of FIG. 11 are complete, the newly exposed surfaces in the tissue may be disinfected, at reference 720 of FIG. 11. Disinfecting the newly exposed surfaces may kill any remaining microbes and, thus, prevent any remaining microbes from forming secondary lesions in the tissue.

In addition, the method may include sealing the newly exposed surfaces, at reference 725 of FIG. 11. The acts of disinfecting at reference 720 and sealing at reference 725 may occur simultaneously. The same material may disinfect and seal the newly exposed surfaces. As a non-limiting example, a solution of 5% glutaraldehyde and 35% hydroxyethyl methacrylate (HEMA) may be applied to the newly exposed surfaces to disinfect and "fix" the hard tissue of a tooth to prepare the tissue to be sealed using glass ionomer. In some embodiments, the lesion may also be filled, at reference 730, in a manner known in the art.

Figure 12A:
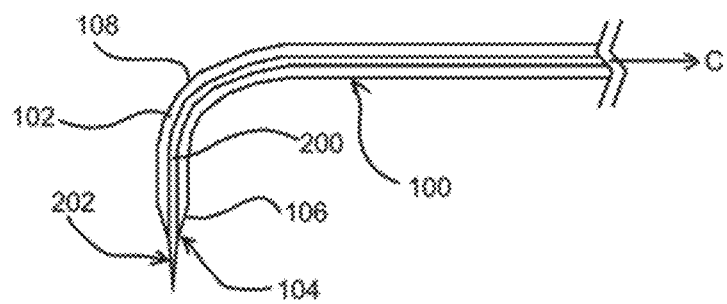
FIGS. 12A to 12C illustrate an embodiment of a diagnostic tool that characterizes a mixed microbial infection.
Figure 12B:
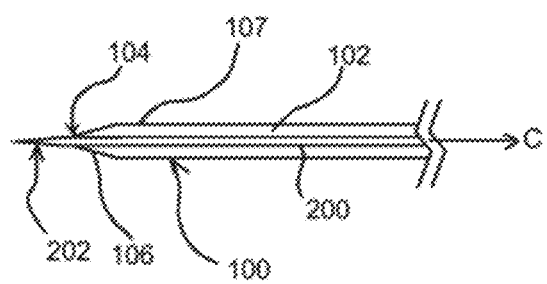
Figure 12C:
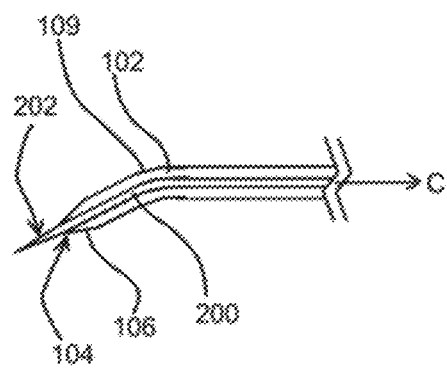

Turning now to FIGS. 12A to 12C, an embodiment of a diagnostic tool or detection device 100 for use in methods detecting viable microbes within hard and soft tissues is illustrated. The detection device 100 may include a hollow interior 102, which may be open at both ends, and a distal end 106 having an aperture 104 disposed at the distal end 106. A sensing tip 202 connected to a conduction cord 200 may by disposed within the hollow interior 102 and may be lengthened or shortened at the will of the user to suit the length of the tip 200 needed for the defined area being addressed (e.g., the lesion, the area surrounding the lesion, a depth of the lesion, etc.). The sensing tip 202 may extend through the aperture 104 at the distal end 106 of the hollow interior 102.

The sensing tip 202 may include one or more sensors for detecting an electrical or chemical signal denoting if viable microbes are present within the defined area. For example, the sensing tip 202 may include a radio frequency (RF) sensor, an ultrasound sensor, a light or optic sensor, a pH sensor, a salinity sensor, or any other appropriate electrical and/or chemical sensor. Additionally, the sensing tip 202 may be capable of detecting the intensity of the signal, which may be represented by color, sound, numerical scale, or another appropriate indication of signal strength. The strength of the electrical or chemical signal may be correlated to the relative estimate of the number of viable microbes present in the defined area.

In some embodiments, the sensing tip 202 may include a sensing mechanism that is configured, selected or otherwise adapted to detect the presence of microbes on or near the sensing tip. More particularly, the sensing tip 202 may include a sensing mechanism that is able to detect and quantify, within an acceptable degree, the presence of living, active or otherwise viable microbes which may generally contribute or be investigated to be contributing to the lesion being dissected and/or examined by the sensing tip 202. In some examples, the sensing mechanism may include a biochemical or electrochemical sensor that produces or is used to produce a signal proportional to or indicative of viable microbe population, concentration and/or ratio of viable to non-viable microbes present.

In some embodiments, the biochemical or electrochemical sensor may include at least one target specific ligand, such as an antibody or nucleic acid (or derivative) aptamer, which may be selected to bind or distinguish between viable and non-viable microbe(s) of interest. In general, binding of the viable microbe(s) to the target specific ligand may generally elicit a conformational change in the molecule or an alteration of its hydration shell which may be utilized to generate a change in electrical potential, Raman scattering, fluorescence or other emission change, or a conformation dependent chemical reaction, such as at the sensing tip. Target specific ligands such as antibodies and/or aptamers may also be selected for species specificity as well as viable vs. non-viable distinguishing. Ligands for different microbes may, for example, be included on different sensing tips, or on different regions of the sensing tip 202.

In other embodiments, the sensing tip 202 may include or be utilized to collect dissected material for analysis ex situ, such as in a tabletop or chairside analysis device, which may, for example, include the sensing mechanism(s) discussed above. The sensing tip 202 may then, for example, be configured to aid a user in collecting the dissected material along with viable and/or non-viable microbes for analysis. In some examples, the sensing tip 202 may include an electrostatic, magnetic, suction, capillary action, reversible adhesion or other collecting mechanism such that dissected material may be attracted to or otherwise gathered and then deposited into a device for analysis The sensing tip 202 may be connected to a computer or other processor for receiving the signals and the intensity of the signals detected by the sensing tip 202. For example, the sensing tip 202 may be connected either directly or indirectly (e.g. direct wire connection for digital or analog signal connection, wireless connection, etc.), to a device performing data collection or analysis, such as through an output C to a computer, cloud device, mobile device or other appropriate device.

The sensing tip 202 may emerge or be coupled to the distal end 106 in a manner that reduces or aids in reducing or eliminating accumulation of microbes or other contaminants such that they do not enter and/or contaminate the hollow interior 102 of the device 100. For example, the sensing tip 202 may be friction fit within the aperture 104 at the distal end 106, providing a tight and sealed connection. Additionally, and/or alternatively, an adhesive or sealant may be employed to seal the distal end 106 and the aperture 104. This may generally be desirable to reduce cross-contamination, such as when using the device 100 sequentially between different portions of the target lesion. The distal end 106 may, for example, taper and/or provide a smooth, jointless or other form of surface or transition to the sensing tip 200 such that microbes or contaminants have no or a reduced surface to which to adhere or intrude. In general, the aperture 104 through which the sensing tip 200 emerges may also provide a seal or other tight interface such that microbes or contaminants are prevented from entering the interior 102, such as during translation of the sensing tip 200 within the interior 102 to extend or retract.

The device 100 may include a portion that is shaped or configured to reach different locations or approaches for a target lesion, as illustrated with the right angled portion 108 in FIG. 12A, the straight portion 107 in FIG. 12B, and the partially angled portion 109 in FIG. 12C. In general, any desirable angle or other shaping may be utilized as may be useful for a particular application. The device 100 may also include a flexible or deformable portion such as to be adjustable to different angles or shaping.

In some embodiments, the sensing tip 202 may be capable of counting and communicating precise counts of the number of viable microbes present, and calculate the number of organisms per milligram of material undergoing dissection as the material is collected, for example, by suction, electric or chemical adhesion, or other, in real time while continuing the dissection. In this embodiment the instrument would be guided by a visual or sound signal sensing the microorganisms present within the tissue, or this could be accomplished robotically.

For example, FIGS. 13A and 13B illustrate another embodiment of the tool of FIGS. 12A-12C in use during a method of treating, excavating, or diagnosing one or more dental lesions. Specifically, the device 100 may include an dissection device 300 and the sensing tip 202 may be a working tip 310, which may be used to collect fragmented or other dissected material 60 which the working tip 310 (or other tool, such as burs or brushes) has separated from the surrounding tissue 90 of a target lesion, such as illustrated with the dissected area 92. For example, the working tip 310 may be electrically charged, magnetic, coated or composed of adhering material, or otherwise configured to gather, attract, or adhere dissected material 60. The dissected material 60 may then be transferred away from the dissected area 92 for further analysis (e.g. weighing, culture, identification, etc.), such as illustrated with the transfer D of the dissected material 60 into a receptacle 70 (e.g. a tube with culture or capture media). The working tip 310 may further be configured to release the dissected material 60, such as by elution, removal of the attractive force, or otherwise. The receptacle 70 may further generally include features to close or seal it against further contamination or entry of additional material to preserve the sample for analysis (e.g. a threaded cap, snap closure, etc.).

In some embodiments, the working tip 310 may also be adapted to release into the receptacle 70, and in general the mass of the working tip 310 would be determined or known prior to release to allow for accurate weighing of the dissected material 60. In a further iteration of the above embodiment, the dissected weighed and collected mixed microbe sample would undergo sequencing analyses to determine genera and species by numbered sequential portions while calculating the percent of each genus, specie, strain and/or other identifier within that portion and generating a lesion map displaying the relative spatial relationship of the microbes as they are harvested portion by portion, and the percentage of microbes present within each portion, along with the total microbe count of the total portions collected FIG. 14 schematically illustrates one example of a system 600 to be used with the tools of FIGS. 12A-12C and 13A-13B in methods of treating, excavating, or diagnosing dental lesions. The system 600 may include a sample handling device 400 connected to an analysis device 500. The system 600 could be used as part of a real-time surgical instrument and/or as a method and instrument to validate efficacy of a treatment, a treatment material, chemical or process. The sample handling device 400 would, for example, after isolation, interface with or include dissection and/or collection mechanisms B to dissect, collect dissected material, record or notate the relative spatial disposition of the collected dissected material (e.g. by layers or portions) for analysis. For example, the collection mechanisms B may include the detection device 100 and/or the dissection device 300.

A user may also manually perform some or all of the dissection and collection of the lesion and areas surrounding the lesion. The dissected material may then be returned to the sample handling device 400, such as through a sample port or receptable 402. The sample handling device 400 may further include additional instruments, attached or integrated devices to perform steps such as weighing samples, culturing viable microbes, quantifying viable microbes (e.g. number per weight of sample or other concentration measurement of viable microbes), and sequencing or otherwise identifying microbes (e.g. through PCR, qPCR, molecular probes, next generation sequencing, etc.), such as through the weighing device 404, the culturing or microbe quantifying device 406, and the identification device 408.

In general, the sample handling device 400 may also contain or interface with sources of reagents, growth media, etc. to perform its tasks, such as shown with reagent storage 410. The output from the various devices may then be transmitted C to an analysis device 500, such as a computer, mobile device, cloud device or service, etc. In general the analysis device 500 may include or output to displays, such as to show gathered data and/or results through a display 502 (e.g. for microbe map(s), viable microbe counts/quantification/percentages, raw data, genus/specie/strain identifications, etc.). The analysis device 500 may further store or be connected to storage for the data and analysis, such as to a memory module or service 504. The analysis device 500 may also include appropriate user interface(s) 506 to allow a user to view/interact/annotate data/results, direct the sample handling device 400, etc.

In some embodiments, the sensing tip 202 may include a sensing mechanism that is configured, selected or otherwise adapted to detect the presence of microbes on or near the sensing tip. More particularly, the sensing tip may include a sensing mechanism that is able to detect and quantify, within an acceptable degree, the presence of living, active or otherwise viable microbes which may generally contribute or be investigated to be contributing to the lesion being dissected and/or examined by the sensing tip. In some examples, the sensing mechanism may include a biochemical or electrochemical sensor that produces or is used to produce a signal proportional to or indicative of viable microbe population, concentration and/or ratio of viable to non-viable microbes present.

Turning now to FIG. 15, a flowchart of a method 800 for validating the efficacy of a purported antimicrobial dental restorative product is illustrated. Such a method 800 may be conducted across a statistically significant sample size (e.g., at least 30 subjects, etc.). The method 800 includes a licensed clinician placing or using a product claiming antimicrobial properties according to manufacturer's directions.

The subject and the restored tissue are then allowed to resume normal activities, at reference 810. After the passage of a predetermined duration of time, at reference 820, the site is re-accessed, at reference 830. In the example of a tooth, re-accessing the site may include removing the "filling" from the tooth.

Upon re-accessing the site, the site may be sampled for microbes at one or more locations, at reference 835, using the systematic aseptic layer-by-layer dissection method described. If no microbes known to be active in dental caries disease are present across a statistically significant sample size, at reference 840, the purported antimicrobial product may be validated as a certified antimicrobial product, at reference 845. If microbes known to be active in dental caries lesions are present, at reference 840, the antimicrobial properties of the purported antimicrobial product may be deemed to be suspect or ineffective, at reference 850.

Features from different embodiments of the disclosed subject matter may be employed in combination. Although the disclosure provides many specifics, the specifics should not be construed as limiting the scope of any of the claims, but merely as providing illustrations of some embodiments of elements and features of the disclosed subject matter that fall within the scopes of the claims. Other embodiments of the disclosed subject matter may be devised that are also within the scopes of the claims. Accordingly, the scope of each claim is limited only by its plain language and the legal equivalents thereto.

What is claimed:

1. A method of characterizing a mixed microbe lesion in hard or soft tissue of a human, veterinary, or botanical subject, comprising:
    preparing an aseptic environment;
    introducing a subject into the aseptic environment;
    aseptically isolating an area surrounding the mixed microbe lesion;
    aseptically and systematically dissecting tissue from the mixed microbe lesion, from an exterior of the mixed microbe lesion toward an interior extent of the mixed microbe lesion, to provide a plurality of samples of the tissue;
    identifying a genus and a species of each viable microbe in each sample of the plurality of samples of the tissue and quantifying each genus and species of each viable microbe in each sample of the plurality of samples of the tissue;
    generating a map of the mixed microbe lesion, including the genus and species and the number of each viable microbe in each sample and a spatial relationship of each sample relative to other samples of the plurality of samples of the tissue; and
    identifying an advancing front of the mixed microbe lesion.

2. The method of claim 1, wherein aseptically isolating the area surrounding the mixed microbe lesion comprises retracting soft tissues away from the mixed microbe lesion.

3. The method of claim 2, wherein retracting soft tissues away from the mixed microbe lesion comprises installing a rubber dam to retract the soft tissues from the mixed microbe lesion and overlaying the rubber dam with a sterile polymer to establish an aseptic operating field.

4. The method of claim 1, further comprising:
    disinfecting the area surrounding the mixed microbe lesion without disinfecting the mixed microbe lesion.

5. The method of claim 1, wherein the mixed microbe lesion comprises a mixed microbe lesion in tissue that can configured to be dried temporarily or partially dried temporarily, (e.g., remain moist).

6. The method of claim 5, wherein aseptically isolating the area surrounding the mixed microbe lesion comprises:
    allowing the area surrounding the mixed microbe lesion to dry in HEPA filtered ambient air; and
    forming a border on the area surrounding the lesion by applying a sterile polymer that can configured to form a seal on a dry surface.

7. The method of claim 6, wherein forming the border comprises forming a dam from a light-polymerized polymer.

8. The method of claim 5, wherein aseptically and systematically dissecting tissue from the mixed microbe lesion comprises dissecting a plurality of layers from the lesion.

9. The method of claim 5, further comprising disinfecting surfaces exposed by aseptically dissecting the lesion.

10. The method of claim 9, wherein disinfecting comprises disinfection of hard surfaces of a tooth only with a solution comprising about 5% glutaraldehyde and about 35% hydroxyethyl methacrylate (HEMA) or disinfection of tissues that ooze or bleed with an antibiotic in powder or solution form.

11. The method of claim 5, wherein the mixed microbe lesion comprises a dental caries lesion in a tooth that can configured to be dried temporarily or in tissues that ooze or bleed such as botanical tissues or animal bone and soft tissues.

12. The method of claim 1, further comprising:
including the map in a library of maps of mixed microbe lesions.

13. The method of claim 12, wherein including the map in the library of maps of mixed microbe lesions comprises including the map in a library of maps of mixed microbe lesions from human, veterinary, or botanical subjects from a common group.

14. The method of claim 13, further comprising:
using the library of maps to develop a treatment regimen for mixed microbe lesions from a same type of tissue among different subjects of the common group.

15. The method of claim 12, further comprising:
tailoring a regimen for treating other mixed microbe lesions in the human, veterinary, or botanical subject or in a population of which the human, veterinary, or botanical subject is a part based on the microbes that caused the mixed microbe lesion.

16. The method of claim 1, further comprising:
applying a purported antimicrobial product to a site from which the mixed microbial lesion was dissected.

17. The method of claim 16, further comprising:
after the passage of a prolonged period of time, re-accessing the site and sampling the site for the presence of microbes.

18. The method of claim 17, further comprising
certifying the purported antimicrobial product as an antimicrobial product 4 when no microbes were present at the site.

19. The method of claim 17, further comprising
identifying the purported antimicrobial product as a suspect antimicrobial product when microbes were present at the site.

20. The method of claim 1, wherein
aseptically and systematically dissecting tissue from the mixed microbe lesion further comprises dissecting a plurality of layers from the lesion; and
wherein generating the map of the mixed microbe lesion, including the genus and species and the number of each viable microbe in each sample and the spatial relationship of each sample relative to other samples of the plurality of samples of the tissue further includes illustrating the spatial relationship of each sample relative to a depth of the lesion and generating a map representing the genus and species and number of each viable microbe in each plurality of layers from the lesion relative to adjacent layers.

\* \* \* \* \*